United States Patent [19]

Schmidt et al.

[11] 4,263,454

[45] Apr. 21, 1981

[54] LITHIUM RIBONATE, LITHIUM ARABONATE AND THE PREPARATION AND PURIFICATION OF THESE SALTS

[75] Inventors: Wolfram Schmidt, Friedelsheim; Joachim Paust, Neuhofen, both of Fed. Rep. of Germany

[73] Assignee: BASF Aktiengesellschaft, Fed. Rep. of Germany

[21] Appl. No.: 100,723

[22] Filed: Dec. 6, 1979

[30] Foreign Application Priority Data

Dec. 6, 1978 [DE] Fed. Rep. of Germany ....... 2852720

[51] Int. Cl.$^3$ .......................................... C07C 59/105
[52] U.S. Cl. .................................................. 562/587
[58] Field of Search ........................................ 562/587

[56] References Cited

U.S. PATENT DOCUMENTS 2,438,882  3/1948  Stembach .......................... 562/587

OTHER PUBLICATIONS

Shirokura, F. et al., Chem. Abstracts, 58230m, vol. 70, 1969.

*Primary Examiner*—Paul J. Killos
*Attorney, Agent, or Firm*—Oblon, Fisher, Spivak, McClelland & Maier

[57] ABSTRACT

Lithium ribonate and lithium arabonate are novel compounds by means of which ribonic acid, required as an intermediate for the synthesis of riboflavin (vitamin $B_2$), or its salts, can be prepared particularly advantageously. The great advantages of the synthesis of ribonic acid are that, surprisingly, mixtures of lithium ribonate and lithium arabonate in aqueous solution can be exceptionally successfully separated into their components be fractional crystallization, and that the desired lithium ribonate, which is the less soluble salt and crystallizes out first, can be isolated in a very pure form. The solution which remains and which in the main contains lithium arabonate can be inexpensively re-epimerized.

2 Claims, No Drawings

LITHIUM RIBONATE, LITHIUM ARABONATE AND THE PREPARATION AND PURIFICATION OF THESE SALTS

FIELD OF THE INVENTION

The present invention relates to lithium ribonate (Ia) and lithium arabonate (Ib) and to processes for the preparation and purification of these salts.

BACKGROUND OF THE INVENTION AND DESCRIPTION OF THE PRIOR ART

It is well-known that ribonic acid and its salts are very important as intermediates for the synthesis of riboflavin (vitamin $B_2$). The ribonates are obtained by oxidizing glucose, in aqueous sodium hydroxide solution or potassium hydroxide solution, by means of oxygen to give a mixture of Na arabonate and Na formate, or K arabonate and K formate, isolating the arabonate from this solution by adding a water-miscible solvent and then epimerizing the arabonate by heating in aqueous solution at 130°–140° C.

Since this epimerization always only proceeds to an equilibrium of about 70% of arabonate and 30% of ribonate, fractional crystallization of arabonate and ribonate is necessary. However, the sodium salts and potassium salts are not suitable for this purpose, since they are extremely water-soluble and furthermore do not differ sufficiently in their solubility. For this reason, the aqueous solutions containing Na or K arabonate and Na or K ribonate are in general mixed with calcium chloride, after which calcium arabonate preferably crystallizes out on cooling (cf. Japanese Published Patent No. 4225/1955). A variant of this method is first to convert the Na arabonate or K arabonate into Ca arabonate, isolate the latter and then carry out the epimerization (cf. U.S. Pat. No. 2,438,882). On fractional crystallization of the said epimeric calcium salts, a ribonate which is about 80% pure can be obtained.

To achieve greater purity, the Ca salts are converted to other salts, which can be purified by further crystallization. Separation methods employing the zinc, calcium and mercury salts have been disclosed, but these are unsuitable for an industrial process because of the toxicity of the metal salts and the resulting problem of disposing of the effluent.

It is true that the iron salts, also used for this purpose, are non-toxic, but they have other important disadvantages. For example, conversion of the calcium salts to the iron salts requires heating for from 3 to 5 hours at 80°–100° C., which is industrially unattractive. Furthermore, conversion of the iron ribonate into ribonolactone gives yields of only about 80–85%, which is unsatisfactory for an industrial method of synthesis.

SUMMARY OF THE INVENTION

It is the object of the present invention to separate ribonate and arabonate from one another by a simpler method than those of the prior art.

We have found the novel compounds lithium ribonate (Ia) and lithium arabonate (Ib) and have further found that the above object can be achieved by an elegant method using these compounds.

DETAILED DESCRIPTION OF THE INVENTION

In accordance with the present invention, it has been found, surprisingly, that mixtures of lithium ribonate (Ia) and lithium arabonate (Ib) present in aqueous solution can be very successfully separate into their components by fractional crystallization, in which the desired less soluble Ia, which crystallizes first, can be isolated in a very pure form. The remaining solution, which in the main contains Ib, can, without great expense, be re-epimerized, which in turn can again be followed by the crystallization according to the invention.

The aqueous solutions containing Ia and Ib are obtained in the conventional manner by epimerizing lithium arabonate by heating an aqueous solution thereof at 130°–140° C., in the presence or absence of a catalytic amount of a base, eg. pyridine, picoline or dimethylamine, or of an inorganic basic ion exchanger, in a neutral or alkaline medium.

Lithium arabonate, like the other alkali metal arabonates, is easily accessible. It is obtained by oxidizing glucose, in an aqueous lithium hydroxide solution by means of oxygen, in the conventional manner, and precipitating the lithium arabonate in a crystalline form from the solution obtained, which contains lithium arabonate and lithium formate, by adding a water-miscible solvent.

A further possible method of obtaining the Li salts is to acidify an aqueous solution of the potassium salts with a mineral acid, such as sulfuric acid, precipitate the potassium salt of the mineral acid by means of a water-soluble organic solvent, for example ethanol, and add lithium hydroxide to the solution which remains. Alternatively, the potassium in the potassium arabonate can be replaced by lithium over a lithium-laden cation exchanger.

The invention relates not only to the novel lithium salts Ia and Ib but also to a process for preparing pure lithium ribonate, wherein an aqueous solution, containing lithium ribonate and lithium arabonate, is mixed with from 40 to 900, preferably from 60 to 300, % by weight, based on the amount of water, of a water-soluble non-ionic or virtually non-ionic organic solvent and the lithium ribonate is then allowed to crystallize from the mixture at from 0° to 20° C. Using this process, it is possible to obtain lithium ribonate in up to 95% purity by a single crystallization. The lithium arabonate, if it is to be used to prepare lithium ribonate, can be directly recycled, in the form of the aqueous solution obtained by distilling off the non-ionic solvent, to an epimerization process.

The invention further relates to a process for the preparation of an aqueous solution of a mixture of lithium ribonate and lithium arabonate, wherein lithium arabonate is epimerized to a mixture of lithium ribonate and lithium arabonate in the conventional manner by heating in aqueous solution at from 130° to 140° C.

For carrying out the fractional crystallization, the aqueous solutions, containing Ia and Ib, are advantageously brought to a concentration corresponding to a total content of from 10 to 60, preferably from 20 to 40, % by weight of epimeric Li salts. The ribonate in general accounts for from about 25 to 30% of the total content of the Li salts (taken as 100%), the remainder being arabonate. However, the process according to the invention can also be used, for example, for the fine purification of the mother liquors which are obtained on fractional crystallization of the epimeric Ca salts and which contain from about 70 to 80% of ribonate and from 20 to 30% of arabonate (cf. Examples 5 and 6).

Depending on the concentration of the lithium salts in the aqueous solution and depending on the nature and amount of the solvent used, the crystallization can be carried out at from 0° to 90° C. Temperatures ranging from ambient temperature to 70° C., more especially from 40° to 70° C., are preferred.

Compared to the separation employing the Ca salts, separation of the epimers via and Li salts has the particular advantage that the lithium ribonate Ia is less soluble than the lithium arabonate Ib. This is advantageous because, if the arabonate is less soluble, as with the calcium salts, it must be substantially crystallized out, by an involved method, so that there should not be too much arabonate remaining in the mother liquor alongside the desired ribonate. Even then, the achievable purity of the ribonate is only about 70–80%. If conversely, as in the case of the lithium salts, the ribonate is less soluble, it suffices to crystallize from about 30 to 60% of the ribonate, in which case a lithium ribonate which is from 95 to 98% pure is obtained.

Suitable organic solvents, for the purposes of the invention, are, in particular, $C_1$–$C_4$-alkanols, eg. methanol, ethanol, isopropanol and n-butanol; cycloaliphatic ethers, eg. dioxane, and alkanediols of 2 or 3 carbon atoms which are partially etherified with methanal or ethanol. Methanol, and ethylene glycol monomethyl ether and monoethyl ether, are particularly suitable. Mixtures of these solvents may also be used.

The solvents are advantageously used in amounts of from 40 to 900, preferably from 60 to 300, % by weight, based on the water.

It is advisable to initiate the crystallization with a few lithium ribonate crystals. Pure lithium ribonate crystallizes from methanol in the form of colorless crystals and melts (with decomposition) at 201° C. Pure lithium arabonate crystallizes from methanol in the form of colorless crystals containing 1 mole of water of crystallization. The compound melts, with decomposition, at 167°–169° C.

The importance of lithium arabonate in particular resides in the fact that it can be converted to lithium ribonate by epimerization in the manner conventionally used for potassium arabonate and sodium arabonate, until the equilibrium (of about 70% of arabonate and 30% of ribonate) is reached, and that the lithium ribonate can, by the method according to the invention, be separated very simply, and in a very pure form, from the non-epimerized lithium arabonate.

Pure lithium ribonate is an important intermediate for the synthesis of riboflavin. For this, it is first converted, in the conventional manner, to ribonolactone by treatment with an acid or an acidic ion exchanger. The compounds according to the invention permit a particularly economical and elegant separation of ribonate and arabonate, and hence achieve a substantial simplification of the total synthesis of riboflavin. This synthesis, using the compounds according to the invention and the process according to the invention, is shown diagrammatically below.

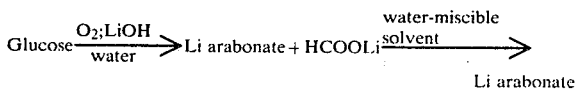

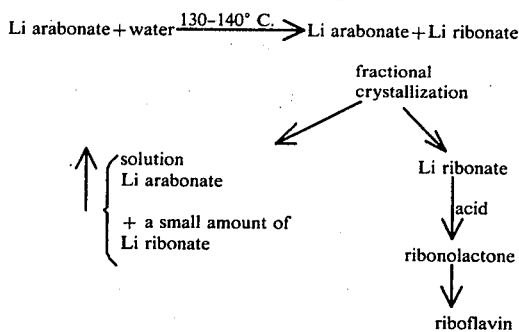

The following examples are intended to further illustrate the invention and should by no means be construed as limiting the scope thereof.

EXAMPLE 1

(a) Preparation of lithium arabonate by oxidation of glucose

A solution of 65 g of glucose and 20 g of LiOH in 650 ml of water was heated under an oxygen pressure of 20 bar for 6 hours at 45°–50° C. About 560 ml of water were then distilled from the reaction mixture, and 210 ml of methanol were added to the solution which remained. 50 g of lithium arabonate crystallized out. The yield was accordingly 90%.

Melting point = 167°–169° C. (with decomposition).

(b) Preparation of lithium arabonate from potassium arabonate

Concentrated sulfuric acid was added to a solution of 41 g of potassium arabonate in 35 ml of water until the pH was about 2. 120 ml of dioxane were then added, whereupon 17 g of crystalline $K_2SO_4$ precipitated. After filtering off the latter, a solution of 5 g of LiOH in 10 ml of water was added to the warm filtrate. After adding a further 80 ml of dioxane, lithium arabonate crystallized out in about 95% yield.

EXAMPLE 2

720 g of dioxane were added to a solution, at 90° C., of 70 g of Li arabonate, 30 g of Li ribonate and 180 g of water, as obtained from the epimerization of 100 g of Li arabonate, and the mixture was subjected to fractional crystallization at 60° C., a few Li ribonate crystals being added. After 1 hour, the crystals were filtered off at 60° C. The yield of 95% pure Li ribonate was 15.5 g (=50%, based on Li ribonate employed).

EXAMPLE 3

400 ml of methanol were added to a solution, at 30° C. of 30 g of Li ribonate, 70 g of Li arabonate and 400 g of water, this solution having been obtained by epimerizing 100 g of Li arabonate by heating the aqueous solution at 130°–140° C., decolorizing with active charcoal and then concentrating the solution, and the mixture was cooled to 0° C. After seeding with a few Li ribonate crystals, 13.5 g of 94% pure Li ribonate crystallized out in the course of 12 hours. This corresponded to a yield of 45%, based on Li ribonate employed for the crystallization.

Melting point 201° C. (with decomposition).

EXAMPLE 4

670 g (700 ml) of ethylene glycol monomethyl ether were added to a solution, at 90° C., of 30 g of Li ribonate, 70 g of Li arabonate and 250 g of water, the solution having been obtained by epimerizing Li arabonate by heating an aqueous solution at 130°–140° C., decolorizing with active charcoal and subsequently concentrating the solution, and the mixture was subjected to fractional crystallization at 60° C. After seeding with Li ribonate, 15 g (=50%, based on Li ribonate employed) of 95% pure Li ribonate crystallized out in the course of 1 hour.

EXAMPLE 5

307 g (320 ml) of ethylene glycol monomethyl ether were added to a solution, at 90° C, of 70 g of Li ribonate, 30 g of Li arabonate and 180 g of water, and the mixture was kept at 60° C. for one hour. In the course thereof, 61 g (=87%) of 95% pure lithium ribonate precipitated.

The starting solution used was the mother liquor obtained on separating out crystalline Ca arabonate from the solution obtained on epimerizing Ca arabonate. The calcium was precipitated from this solution as calcium sulfate by means of sulfuric acid, and the solution which remained, and contained the epimeric acids, was converted to a corresponding lithium salt solution by means of lithium hydroxide, and then concentrated.

EXAMPLE 6

330 g of methanol were added to a solution, at 30° C., of 70 g of Li ribonate, 30 g of Li arabonate and 180 g of water, the solution having been obtained similarly to the starting solution described in Example 5 by epimerizing calcium arabonate, separating off crystalline calcium arabonate and then converting the calcium salts of the resulting mother liquor into the lithium salts, and the mixture was left to stand at 0° C. for 1 hour. In the course thereof, 62 g (=88%) of 98% pure lithium ribonate crystallized out.

What is claimed and intended to be secured by U.S. Letters Patent is:
1. Lithium ribonate.
2. Lithium arabonate.

* * * * *